United States Patent [19]
Weems

[11] Patent Number: 6,037,182
[45] Date of Patent: Mar. 14, 2000

[54] METHOD FOR DETECTING A LOCATION OF CONTAMINANT ENTRY IN A PROCESSING FLUID PRODUCTION AND DISTRIBUTION SYSTEM

[75] Inventor: John A. Weems, San Antonio, Tex.

[73] Assignee: VLSI Technology, Inc., San Jose, Calif.

[21] Appl. No.: 08/999,296

[22] Filed: Dec. 29, 1997

[51] Int. Cl.$^7$ .................................................. G01N 33/20
[52] U.S. Cl. ................................ 436/75; 436/73; 436/77; 436/79; 436/80; 436/81; 436/82; 436/83; 436/84; 436/149; 436/155; 436/164; 436/172; 436/173; 436/182
[58] Field of Search .................................. 436/73, 75, 77, 436/79–84, 149, 155, 164, 172, 173, 181, 182

[56] References Cited

U.S. PATENT DOCUMENTS

5,369,033  11/1994  DiMilia et al. ........................... 436/148

FOREIGN PATENT DOCUMENTS

4-147060  5/1992  Japan .
7-174676  7/1995  Japan .
9-270411  10/1997  Japan .

OTHER PUBLICATIONS

A. Corradi et al. *J. Crystal Growth* 1988, 89, 39–42.
H.J. Rath et al. *Proc.–Electrochem, Soc.* 1990, 90–11, 335–352.
T.T.H. Fu et al. *Proc–Inst. Environ. Sci.* 1992, 38th, 348–352.
N. Streckfuss et al. *Fresenius' J. Anal. Chem.* 1991, 343, 765–768.
P. Eichinger et al. *Proc.–Electrochem. Soc.* 1993, 93–15, 240–251.
L. Jastrzebski et al. *J. Electrochem. Soc.* 1993, 140, 1152–1159.
H. Shimizu et al. *Jpn. J. Appl. Phys., Part 1* 1993, 32, 3775–3779.
L. Fabry et al. *Fresenius' J. Anal. Chem.* 1994, 349, 260–271.
J.J. Lee et al. *Mater. Res. Soc. Symp. Proc.* 1995, 386, 143–149.
N. Streckfuss et al. *Proc.–Inst. Environ. Sci.* 1995, 41st, 147–154.
L. Jastrzebski et al. *Mater. Res. Soc. Symp. Proc.* 1995, 354, 405–417.
D.C. Grant et al, *J. Inst. Environ: Sci* 1996, 39, 29–37.
S. Biswas et al, in "Ion Implant. Technol.–96, Proc. Int. Conf." 11th 1997 E. Ishida, ed., Institute of Electrical and Electronics Engineers 245–248.
D. Xu et al. *Semicond. Pure' Water Chem. Conf.* 1997, 16th, 31–48.
A. L. P. Rotondaro, et al, Impact of Fe and Cu Contamination of the Minority Lifetime of Silicon Substrates, *Journal of the Electrochemical Society*, vol. 143, No. 9, Sep. 1996, pp. 3014–3019.
Technical Summary: Lifetime and Diffusion Length Measurements to Determine Contamination and Defects in Semiconductors, Charles Evans & Associates, 301 Chesapeake Drive, Redwood City, California 94063.
Evaluation of Conamination and Defects in Semiconductors: Using Lifetime and Diffusion Length Measurement Technique, Charles Evans & Associates, 301 Chesapeake Drive, Redwood City, California 94063.

*Primary Examiner*—Arlen Soderquist
*Attorney, Agent, or Firm*—Douglas L. Weller

[57] ABSTRACT

A method is used to detect a location of contaminant entry in a processing fluid production and distribution system. A wafer is placed in a clean container. The clean container is connected to a test point within the processing fluid production and distribution system. Processing fluid from the test point of the processing fluid production and distribution system is allowed to flow through the clean container. The wafer is dried. The wafer is then tested for the existence of contaminants.

11 Claims, 2 Drawing Sheets

METHOD FOR DETECTING A LOCATION OF CONTAMINANT ENTRY IN A PROCESSING FLUID PRODUCTION AND DISTRIBUTION SYSTEM

BACKGROUND

The present invention concerns the processing of semiconductor wafers and pertains particularly to determining the source of contamination introduced during wafer processing.

During the course or processing semiconductor wafers, processing fluids, such as ultrapure water, are used for a variety of purposes, including cleaning the wafers. In order to produce processing fluid without contaminants, sophisticated processing fluid production systems are used. These processing fluid production systems virtually eliminate contaminants from water.

Occasionally within the processing fluid production system or within the distribution system of the processing fluid, impurities can be introduced. Contaminants, even at a concentration of one part per trillion, can have a negative impact on wafer processing. When contaminants are introduced into a processing fluid production and transportation system it is necessary to locate the source of contamination and correct the contamination problem.

One method of detection of contamination is to sample the processing fluid at various locations within the processing fluid production and transportation system. The sampled fluid can be analyzed to determine contaminant concentrations. However, existing methods to directly measure fluid for contamination concentration are generally not sensitive enough to reliably detect the part per trillion levels of contaminants which are sufficient to disrupt the processing of wafers. It is desirable therefore to discover a better way to detect contaminant concentrations within a processing fluid production and transportation system.

SUMMARY OF THE INVENTION

In accordance with the preferred embodiment of the present invention, a method is presented for detecting a location of contaminant entry in a processing fluid production and distribution system. A wafer is placed in a clean container. For example, more than one wafer may be used. Also, in order to prevent contamination, the wafer is placed in the clean container while the clean container is in a clean room environment.

The clean container is connected to a test point within the processing fluid production and distribution system. For example, connection is achieved using well rinsed tubing.

Processing fluid from the test point of the processing fluid production and distribution system is allowed to flow through the clean container. For example, the processing fluid from the test point of the processing fluid production and distribution system flows through the clean container for at least ten minutes.

The wafer is then dried. This is done, for example, by first shutting off processing fluid flow through the clean container. The clean container is then transported to a clean environment without emptying processing fluid remaining within the clean container. In the clean environment, the remaining processing fluid is emptied from the clean container. The wafer is then dried, for example using an isopropyl alcohol (IPA) dryer.

The wafer is then tested for contaminants. Testing of the wafer may be performed, for example, by oxidizing the wafer in a furnace and then measuring minority carrier lifetimes within the wafer.

Alternatively, testing of the wafer may be performed directly, for example, by measuring contaminants on the wafer using a vapor phase decomposition/total x-ray fluorescence test.

Alternatively, testing of the wafer may be performed directly, for example, by using a vapor phase decomposition/inductively coupled plasma/mass spectrometry test.

The method can be repeated using a different test point within the processing fluid production and distribution system in order to determine where contaminants enter the processing fluid production and distribution system. The processing fluid is, for example, ultrapure water. Alternatively, the processing fluid may be nitrogen, oxygen, sulfuric acid, hydrogen peroxide or another fluid used in processing.

The present invention provides a way to accurately and reliably locate where contaminants enter the processing fluid production and distribution system. The use of test wafers to find contaminants is particularly advantageous as the invention particularly detects those contaminants which stick to wafers and may be detrimental to processing.

DESCRIPTION OF THE PREFERRED EMBODIMENT

Figure 1:
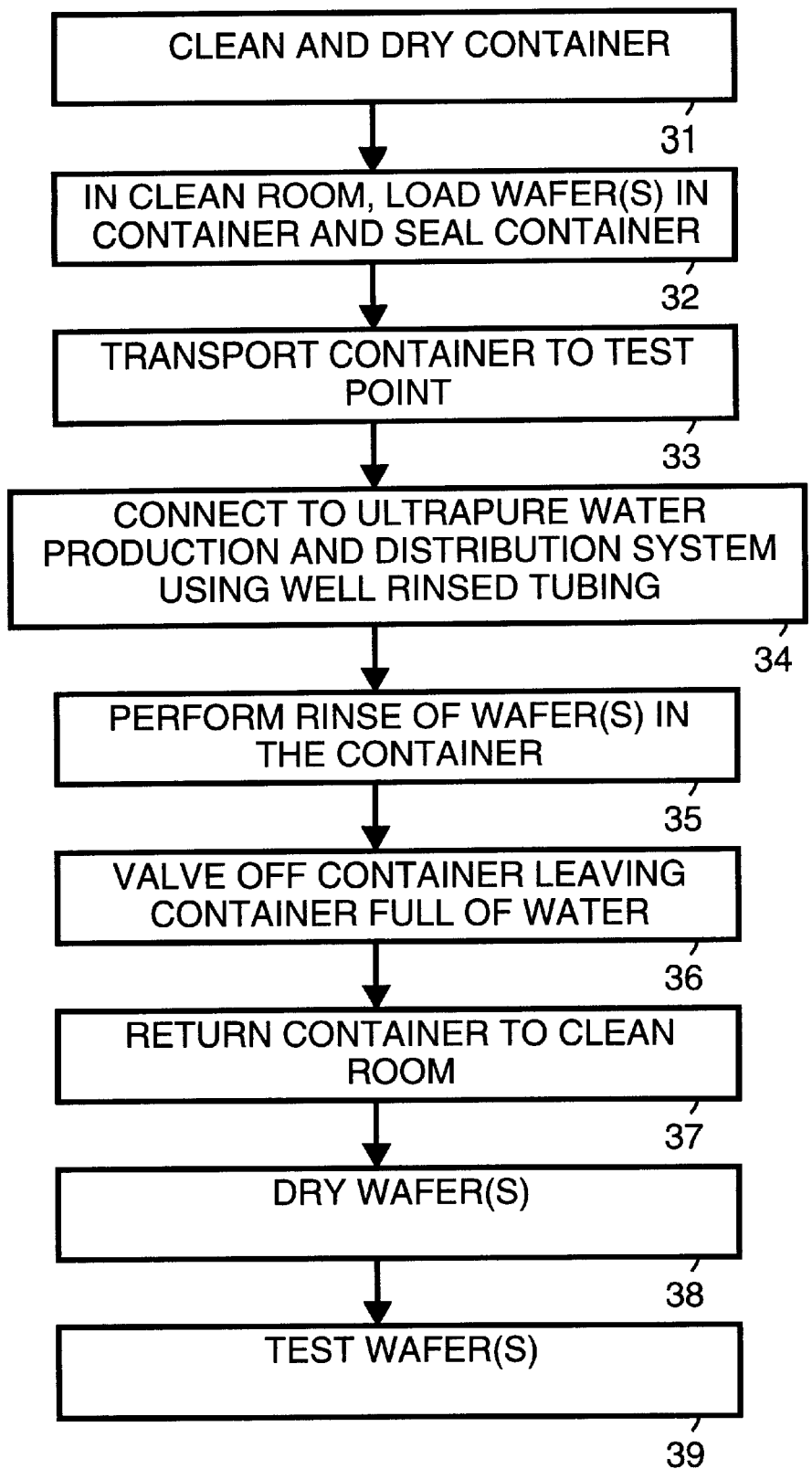
FIG. 1 is a flowchart which illustrates a method for detecting a location at which contamination is introduced into a processing fluid production and distribution system in accordance with the preferred embodiment of the present invention.

FIG. 1 is a flowchart which illustrates a method for detecting a location at which contamination is introduced into a processing fluid production and distribution system in accordance with the preferred embodiment of the present invention.

Figure 2:
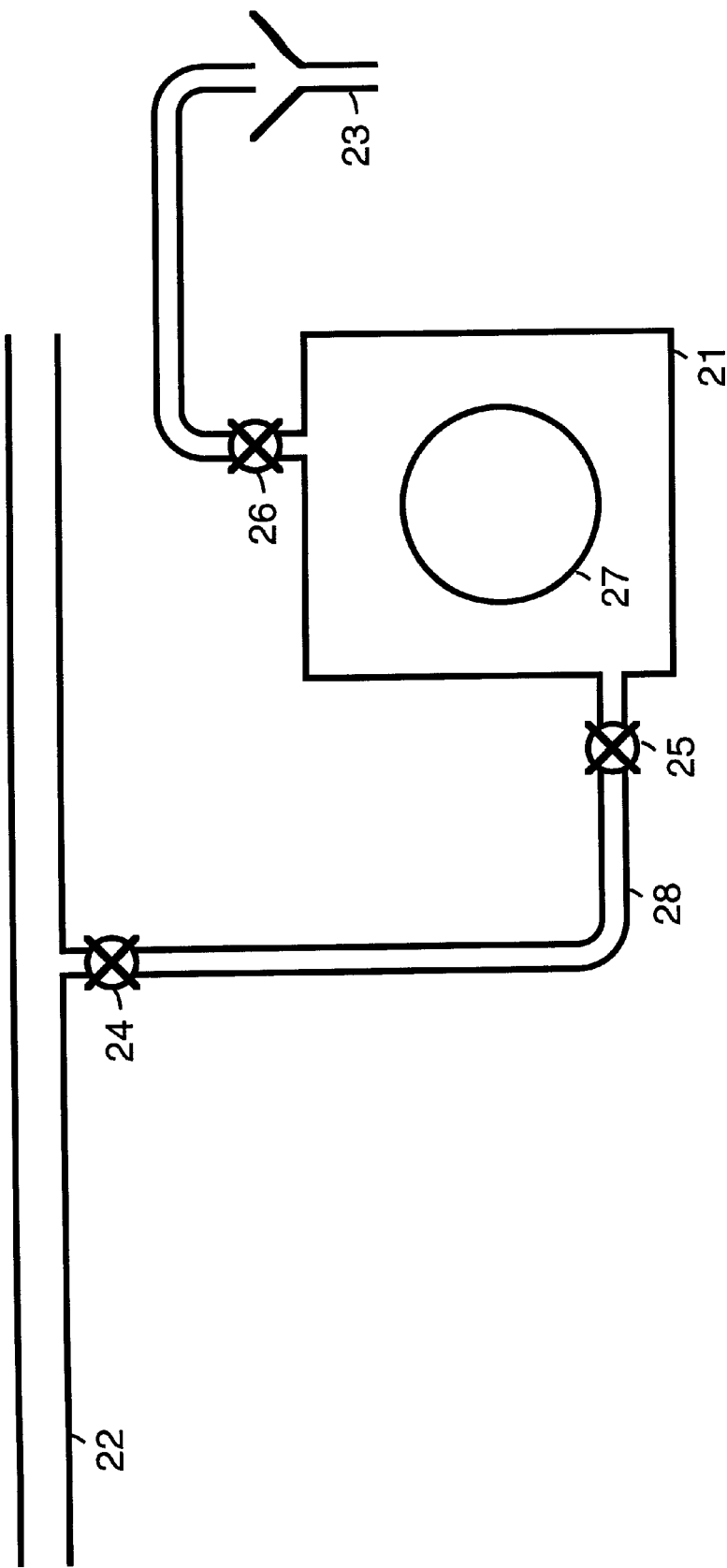
FIG. 2 shows a clean container connected to a processing fluid production and distribution system in accordance with the preferred embodiment of the present invention.

In a step 31, a clean container 21 is cleaned and dried. Clean container 21 is shown in FIG. 2. Clean container 21 is constructed of clean materials such as Teflon, a perfluoralkoxy (PFA) polymer or polyvinylidene fluoride (PVDF).

In a step 32, one or more wafers are loaded into clean container 21. For example the wafer(s) is/are made of silicon. Alternately, the wafer(s) may be made out of any material used for the production of semiconductors. In FIG. 2, the wafer(s) placed in clean container 21 is/are represented by a wafer 27.

Step 32 is performed in a clean room to prevent the introduction of any contamination into clean container 21. After the wafer(s) has/have been placed in clean container 21, clean container 21 is sealed.

In a step 33, clean container 21 is transported to a test point within a processing fluid production and distribution system. In FIG. 2, the processing fluid production and distribution system is represented by a processing fluid pipe 22.

In a step 34, clean container 21 is connected to processing fluid production and distribution system 22 at the test point using well rinsed tubing 28. To control processing fluid flow into and out of clean container 21, a valve 24, a valve 25 and a valve 26 are placed as shown in FIG. 2. A drain 23 is used to dispose of processing fluid which has flowed through and out of clean container 23.

In a step 35, a rinse is performed of wafer(s) 27 within clean container 21. The processing fluid from processing fluid production and distribution system 22 bathes wafer(s) 27 in a clean up-flow pattern allowing any contaminants in the processing fluid from processing fluid production and distribution system 22 deposit onto wafer(s) 27. Typically the processing fluid from processing fluid production and distribution system 22 is allowed to flow through clean container 21 for at least 10 minutes allowing an abundant time for any contaminants in the processing fluid to deposit onto wafer(s) 27.

In a step 36, valve 25 and valve 26 are shut, leaving clean container 21 full of processing fluid.

In a step 37, clean container 21 is returned to a clean room. For example, the clean room is a wet station in the fab.

In a step 38, within the clean room, clean container 21 is opened. Wafer(s) 27 is/are then dried, for example, in an isopropyl alcohol (IPA) dryer.

In a step 39, after drying, wafer(s) 27 are analyzed for trace contaminants. Wafer(s) 27 can be analyzed using one or more available methods. For example, the surface of wafer(s) 27 can be oxidized in a furnace and the minority carrier lifetime can be measured. See, for example, A. L. P. Rotondaro, et al, Impact of Fe and Cu Contamination of the Minority Lifetime of Silicon Substrates, *Journal of the Electrochemical Society*, Volume 143, No. 9, September 19196, pp. 3014–3019.

Alternatively, the contaminants on wafer 27 can be directly measured using a vapor phase decomposition/total x-ray fluorescence test (VPD/TXRF). See for example, *Technical Summary: Lifetime and Diffusion Length Measurements to Determine Contamination and Defects in Semiconductors*, Charles Evans & Associates, 301 Chesapeake Drive, Redwood City, Calif. 94063.

Alternatively, the contaminants on wafer 27 can be directly measured using a vapor phase decomposition/inductively coupled plasma/mass spectrometry test (VPD/ICP-MS). Such testing is performed, for example, by Balazs Analytical Laboratory, having a business address of 252 Humboldt Court, Sunnyvale, Calif. 94089, as well as by other laboratories.

By performing the above described testing at several test points along processing fluid production and distribution system 22 it is possible to determine at what point contamination enters into processing fluid production and distribution system 22. This identification of an entry point of contaminants allows for correction of the system failure.

The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

I claim:

1. A method for detecting a location of contaminant entry in a processing fluid production and distribution system, the method comprising the steps of:
   (a) placing a wafer in a clean container;
   (b) connecting the clean container to a test point within the processing fluid production and distribution system;
   (c) allowing processing fluid from the test point of the processing fluid production and distribution system to flow through the clean container;
   (d) drying the wafer, including the following substeps:
      (d.1) shutting off processing fluid flow through the clean container,
      (d.2) transporting the clean container to a clean environment without emptying processing fluid within the clean container,
      (d.3) in the clean environment emptying the processing fluid from the clean container, and
      (d.4) completely drying the wafer using an isopropyl alcohol dryer; and,
   (e) testing the wafer for existence of contaminants.

2. A method as in claim 1 wherein step (a) is performed in a clean room.

3. A method as in claim 1 wherein in step (a) the wafer comprises silicon.

4. A method as in claim 1 wherein in step (a) more than one wafer is placed in the clean container.

5. A method as in claim 1 wherein step (b) is performed using well rinsed tubing.

6. A method as in claim 1 wherein in step (c) the processing fluid from the test point of the processing fluid production and distribution system flows through the clean container for at least ten minutes.

7. A method as in claim 1 wherein step (e) includes the following substeps:
   (e.1) oxidizing the wafer in a furnace; and,
   (e.2) measuring minority carrier lifetimes within the wafer.

8. A method as in claim 1 wherein step (e) includes measuring contaminants on the wafer using a vapor phase decomposition/total x-ray fluorescence test.

9. A method as in claim 1 wherein step (e) includes measuring contaminants on the wafer using a vapor phase decomposition/inductively coupled plasma/mass spectrometry test.

10. A method as in claim 1 wherein performance of steps (a), (b), (c), (d) and (e) are repeated using a different test point within the processing fluid production and distribution system.

11. A method as in claim 1 wherein the processing fluid is ultrapure water.

* * * * *